United States Patent [19]
Fitzpatrick et al.

[11] Patent Number: 6,121,008
[45] Date of Patent: *Sep. 19, 2000

[54] CHROMATOGRAPHIC IMMUNOASSAY DEVICE AND METHOD UTILIZING PARTICLE VALENCY FOR QUANTIFICATION

[75] Inventors: Judith Fitzpatrick, Tenafly, N.J.; Regina B. Lenda, Wesley Hills, N.Y.

[73] Assignee: Serex, Inc., Maywood, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/821,086

[22] Filed: Mar. 20, 1997

Related U.S. Application Data

[63] Continuation-in-part of application No. 08/618,571, Mar. 20, 1996, abandoned.

[51] Int. Cl.$^7$ .................. G01N 33/543; G01N 33/558
[52] U.S. Cl. .................. 435/7.9; 422/55; 422/56; 422/57; 422/58; 435/7.2; 435/7.93; 435/183; 435/287.1; 435/287.2; 435/287.7; 435/805; 435/810; 435/968; 435/969; 435/970; 435/971; 435/973; 435/975; 436/512; 436/514; 436/518; 436/525; 436/534; 436/810
[58] Field of Search .................. 422/55, 56, 57, 422/58, 60; 435/7.2, 7.9, 7.93, 183, 188, 805, 968, 969, 970, 971, 973, 975, 287.1, 287.2, 287.7, 810; 436/512, 518, 525, 534, 810, 514

[56] References Cited

U.S. PATENT DOCUMENTS

| | | |
|---|---|---|
| 3,817,337 | 6/1974 | Panak et al. . |
| 4,069,105 | 1/1978 | Singh . |
| 4,318,707 | 3/1982 | Litman et al. . |
| 4,323,507 | 4/1982 | Leung et al. . |
| 4,341,866 | 7/1982 | Yoshida . |
| 4,434,236 | 2/1984 | Freytag . |
| 4,480,042 | 10/1984 | Craig et al. . |
| 4,504,413 | 3/1985 | Khanna . |
| 4,551,426 | 11/1985 | Freytag et al. . |
| 4,590,278 | 5/1986 | Edwards et al. . |
| 4,766,064 | 8/1988 | Williams et al. . |
| 4,803,170 | 2/1989 | Stanton et al. ................ 436/518 |
| 4,977,077 | 12/1990 | Ngo et al. . |
| 5,009,998 | 4/1991 | Chow et al. . |
| 5,084,398 | 1/1992 | Huston et al. ................ 436/535 |
| 5,137,808 | 8/1992 | Ullman et al. . |
| 5,164,504 | 11/1992 | Walling et al. . |
| 5,177,021 | 1/1993 | Kondo . |
| 5,183,740 | 2/1993 | Ligler et al. . |
| 5,188,939 | 2/1993 | Mangold et al. . |
| 5,229,073 | 7/1993 | Luo et al. ................ 422/56 |
| 5,330,715 | 7/1994 | Blake et al. . |
| 5,451,504 | 9/1995 | Fitzpatrick et al. . |
| 5,753,517 | 5/1998 | Brooks et al. . |

FOREIGN PATENT DOCUMENTS

| | | |
|---|---|---|
| 2 191 577 | 12/1987 | United Kingdom . |
| WO 89/05978 | 6/1989 | WIPO . |
| WO 91/19980 | 12/1991 | WIPO . |
| WO 93/03175 | 2/1993 | WIPO . |
| WO 93/15230 | 8/1993 | WIPO . |
| WO 94/24563 | 10/1994 | WIPO . |

OTHER PUBLICATIONS

Steward et al., "The Importance of Antibody Affinity in the Performance of Immunoassays for Antibody," *Journal of Immunological Methods*, vol. 78, pp. 178–190, (1985).

*Primary Examiner*—Christopher L. Chin
*Attorney, Agent, or Firm*—Arnall Golden & Gregory, LLP

[57] ABSTRACT

A method and device are provided for the semi-quantitative and quantitative determination of an analyte in a sample. A non-competitive trap which can bind unreacted labelled receptor to analyte but has virtually no binding capabilities to receptor in the presence of analyte is used. Labelled receptor:analyte complex is trapped in a second trap. The relative amounts of unbound receptor in the non-competitive trap versus the amount of receptor:analyte complex in the second trap is a measure of the amount of analyte in the sample.

26 Claims, 4 Drawing Sheets

INCREASING VALENCE IN TRAP II INCREASES ABILITY TO INTERACT WITH LOW VALENCE GOLD PARTICLES I.E., PARTICLES COATED WITH ANTI-THEOPHYLLINE ANTIBODY.

| µg/ml Theophylline | CPDMX | CPDMX on Latex |
|---|---|---|
| 0 | 0.022 | 0.028 |
| 3 | 0.034 | 0.332 |

CHROMATOGRAPHIC IMMUNOASSAY DEVICE AND METHOD UTILIZING PARTICLE VALENCY FOR QUANTIFICATION

This application is a CIP of U.S. Ser. No. 08/618,571, filed May 10, 1996, now abandonded.

BACKGROUND OF THE INVENTION

This invention relates to methods and devices for carrying out immunodiagnostic assays. More specifically, the invention relates to methods and devices involving the use of chromatographic membranes, strips or gels through which sample, analyte, and reagents may move. The invention relates specifically to a chromatographic diagnostic test device for immunochemically determining the presence or amount of an analyte through the use of a multivalent mobile receptor particle and a trapping agent located in the path of moving sample, analyte, and reagents. More specifically still, it relates to a non-competitive assay through the use of a non-competitive trapping agent having a low affinity for unreacted receptor, thereby enabling the separation of bound from unbound receptor and enabling quantitation or semi-quantitation of the bound and/or unbound receptor.

The use of specific binding reagents has proven to be very useful in diagnostic assays and other applications. Such assays involve the detection and determination of an analyte in a sample by causing the analyte to selectively bind or react with a receptor capable of binding to the analyte in the presence of potentially interfering substances. These specific binding receptors form the basis for detection systems that are in widespread use in the art.

The visualization of the results of specific binding reactions is often facilitated by employing one member of the specific analyte-receptor binding pair in labelled form in order that the binding reaction may be indirectly measured by detecting the location and intensity of the label. Useful labels include radiolabels, chromophores, fluorophores, enzymes, magnetic or latex particles, and colloidal gold, the presence of which may be detected by means of various detectors such as gamma counters, spectrophotometers or the naked eye.

Immunoassay devices which generally include a chromatographic membrane, a sample receiving zone, and a labelled receptor for the analyte impregnated in the membrane are well-known in the art. In use, a sample liquid such as urine, blood, serum or other biological fluid suspected of containing an analyte is added to the device. The analyte in the sample reacts with its specific receptor and is captured. The capture event is manifested on the strip in a manner determined by its design and the location and type of reagents used in the assay. The presence or absence, but not the amount of analyte, is then determined by correlating the reaction with the receptor with some standard. Such assay devices properly configured can provide rapid and generally reliable results, but suffer from a variety of restrictions which limit their acceptability and widespread use.

In the field of diagnostic testing, the art has evolved from the use of complex radioimmunoassays and enzyme immunoassays to the use of single card or strip-type devices, either of a unitary, single piece type or having overlapping components. In general, the art has sought to increase the readability of such devices, to eliminate the need for instruments and to shorten the test time so that one may make a determination of the analyte under on-site conditions.

The art has also attempted to reduce the number of steps required to conduct the test to increase the simplicity and convenience of the system. Attempts have been made to produce semiquantitative, non-instrument based immunochemical assays for on-site use but such devices have not been satisfactory for various reasons. For example, they may not be economical to manufacture or the method might be too technique-dependent to be reliably performed by laboratory trained personnel, or the read-out may not be simple enough for on-site use, and/or sample collection. In addition, there often is a need for accurate measurement of volume applied sample when quantitative or semiquantitative results for on-site assays are required. The art would greatly benefit from a semiquantitative or quantitative assay which does not require any measuring of volume of sample, yet can be manufactured economically and provide quantitation of the analyte on the test device itself requiring no instrumentation or extrinsic reading assistance.

SUMMARY OF THE INVENTION

Devices including a sample receiving area or zone, a mobilization zone located distal to or downstream of the sample receiving zone including labelled receptor having specific binding capabilities to the analyte, and downstream of that, a trap for unbound receptor (reland trap), followed by one or more traps for partially or fully bound receptor, are described. Any one or all of the traps may provide the means by which the results of the assay are read. The non-competitive reland trap will bind unbound receptor, but will not bind receptor which has reacted with analyte and will not compete off analyte from bound receptor complexes.

The device in its simplest form further illustrates the concepts. In general, the devices are used by (a) providing a liquid sample to the sample receiving zone and allowing the sample to pass into the mobilization zone containing a labelled receptor for the analyte, such as an antibody. If analyte is present in the sample, it will react with the labelled receptor to form labelled immune complex. Since labelled receptor is preferably used in large excess at the mobilization zone, there may be unreacted labelled receptor even if analyte is present. If analyte is absent, there will be no reaction with the receptor, leaving only unreacted labelled receptor. In either case, the sample will continue through the chromatographic medium moving with it the unbound and bound labelled receptor, if any, to the reland trap for unbound receptor. It is at this point that the selective properties of the reland trap are utilized to initially distinguish between the unbound labelled receptor and the bound labelled complex obtained from the reaction of analyte with its labelled receptor. The reland trap will not react with bound receptor sufficiently to retain it in this zone and, thus, will permit virtually all of the bound complex to move past the immobilized reland trap to a location further downstream. When and if all receptor is bound, there would be very little or no visual event occurring at the immobilized reland trap zone. The trap may be said to be invisible to the transported reaction product of analyte with labelled receptor. On the other hand, the reland trap will react with unreacted labelled receptor and trap the labelled material at that zone. Thus, the immobilized trap for labelled unbound receptor may act as part of the detection zone since it provides the site for the label to accumulate. When the sample contains analyte in an amount which is insufficient to bind a labelled receptor, there will be a color accumulation at the reland trap as well as at a further downstream trap designed to trap the labelled immune complex, i.e. the bound material.

The reaction can be quantitated in several ways. The reland trap may be constructed to present read-out lines corresponding to the column of a thermometer, the height of the color intensity of which is inversely proportional to the amount of the analyte in the sample. Alternatively, the reland trap may be read visually or by an instrument such as a reflectometer by comparison of two or more blocks of color to provide semiquantitation, or the unbound or bound traps may have a built-in control where antibody is detected as either bound or unbound and the relative amounts of each are compared.

In a further embodiment, multiple traps are utilized which bind receptor on particles, preferably gold or latex particles having coupled thereto four to fifty or more receptors, most preferably antibodies, as a function of the relative number of unbound receptor molecules, or "valence". For example, a "ladder trap" can include a reland trap which binds particles having none or only one to two of several receptor molecules occupied by analyte, a trap utilizing ligands with affinity to analyte or a competitive ligand which binds particles having a higher number of receptor molecules bound, an immunogen affinity trap which binds particles having most receptor molecules bound by analyte, for example, and an anti-antibody trap, which binds all particles, even with 100% of the receptor binding sites occupied. The advantage of this embodiment is that it can serve as a highly sensitive, semi-quantitative dipstick since the system is the most responsive to valence. The reland trap is an effective trap because the low affinity of the reland is compensated for by the high avidity of the multivalent receptor coated particle. This principle of balancing affinity against avidity can be utilized to enable traps to further quantitiate the particles that do not bind to the reland trap. Quantitative trapping of bound antibody is possible because a receptor coated particle is a multivalent receptor, for example, in the case of 20 to 30 nm gold particles carrying between about 40 to 100 receptor sites, i.e., having a valence of between 40 and 100. Binding of analyte decreases valence in proportion to the amount of analyte in the sample. Decrease in valence decreases the affinity of the particle for trap material. This loss of affinity for the trap can be overcome by use of traps of increasing the affinity. Thus one can visually separate the particles passing through the reland trap (because they have bound analyte) into several populations by valence which represents the number of analyte molecules bound to the particle. Particles having the most bound analyte will have the lowest valence and will migrate to the traps with the highest affinity.

In one embodiment, a series of traps of increasing affinity/avidity is provided. The avidity of these traps is influenced very little by concentration or small changes in affinity but greatly influenced by valence or avidity. This allows one to build a thermometer with different traps, each trap binding particles which carry a larger number of analyte. For example, the first and lowest avidity trap can be reland on a protein and the second trap can be a reland *protein on latex. The third and fourth trap can be a ligand with an affinity similar to that of analyte, i.e., a competitive ligand, provided in two very different valences or avidities, i.e., on protein and on latex. For traps five and six one can use a ligand with a much higher affinity for receptor, such as an immunogen ligand and linker, which generally have two to three logs higher affinity for the receptor than the analyte on protein and latex. For the seventh and eighth trap one can capture particles with little or no valence using antibody and even this trap can be manipulated to yield zones by using traps of increasing affinity and valence.

Since definitive quantitation is obtained in the bound traps, none of the reagents needs to be present in precisely controlled, critical or stoichiometric amounts as is the case with competitive assays. In addition, manufacture is greatly simplified and becomes relatively inexpensive, resulting in immunochemical test devices which are affordable for on-site use in the field without the need of an instrument. Measuring of the test liquids by the operator is not required when the preferred embodiment of a laminated structure is employed, yielding a semiquantitative or quantitative determination of the level of analyte in the sample. In this preferred embodiment, the strip is occluded by lamination on virtually all surfaces save one accessible sample area, thus ensuring adequate contact of the traps with the sample fluid and providing the basis for a quantitative or semiquantitative assay. In addition, lamination minimizes contamination by environmental fluids or handling. This allows the strip to be dipped into a container of fluid without concern as to the level of fluid in the container and, thus, avoid any handling of the sample or disposal of human infectious material as is required with a dropper. A further advantage is the increased dynamic range of the present non-competitive assay method which, among things, eliminates sample dilutions for quantitation.

BRIEF DESCRIPTION OF THE DRAWINGS

FIG. 6 is a graph demonstrating the increase in ability of a trap to interact with low valence gold particles as a function of increasing valence.

DETAILED DESCRIPTION OF THE INVENTION

The devices described herein are characterized by unique aspects for separating unbound labelled receptor from bound labelled receptor (if any) and utilizing the color or relative color changes obtained to determine the presence, quantitative or semiquantitative amount of analyte. In a preferred embodiment, the quantitative and semiquantitative determinations are facilitated through transport of sample and other reactive materials through a chromatographic strip or membrane which has been laminated between two non-permeable surfaces. Lamination forces the materials to flow through a length of the medium rather than to pool or slid along the top surface of the strip which is critical to enabling a quantitative strip. The amount of analyte is determined by reaction with one or more "traps" to create a color or other detectable change at the site of the trap, which is correlated with the presence or amount of analyte.

To facilitate understanding, the device is discussed herein with respect to the device design, the receptor and label components, and the traps: reland trap, competitive analyte trap, immunogen affinity trap, and anti-antibody trap.

Device Design

Reference to the drawings will illustrate specific embodiments and characteristics of the devices described herein. It will be apparent to those skilled in the art that there are numerous combinations of elements which may be employed to construct variations of those shown.

The devices include a strip having a sample receiving means, a mobilization zone including labelled receptor to analyte located downstream from the sample means, an immobilized reland trap downstream of the mobilization zone, optionally, additional traps for particles having a higher percentage of bound receptor than is bound by the reland traps, and a zone for detection of bound receptor.

In preferred embodiments, the device contains one or more additional detection zones downstream of the immobilized reland trap to react with the labelled reacted immune complex resulting from the reaction of analyte with the labelled receptor which passes through the reland trap. These detection zones can be in any suitable form such as immobilized bands on the strip with appropriate spacing or they may be in the form of homogeneously impregnated blocks or other designs of reagent. In any case, the extent to which the reagents on the lines or block react and change color, or cause a color change, will be a measure of the quantity of analyte present in the sample. One need simply compare the level at which color ends to a scale provided on the device, or separately if desired, to determine concentration.

Figure 1:
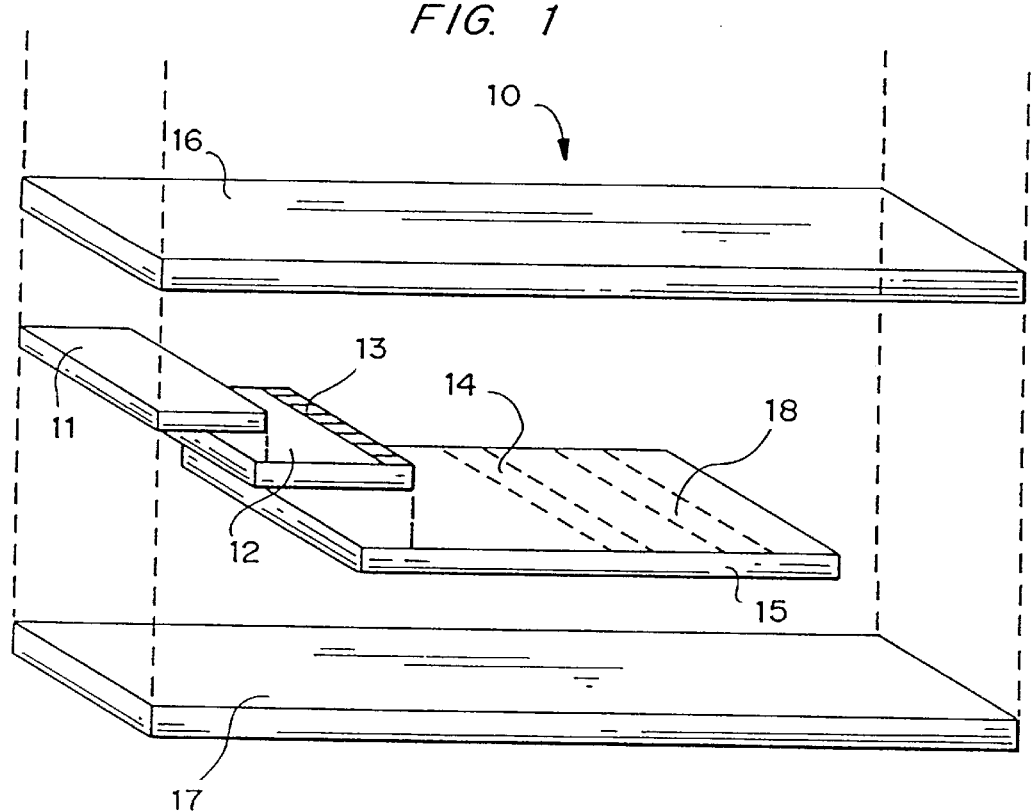
FIG. 1 is a drawing of one embodiment of the present invention before use in exploded perspective view.

FIG. 1 shows one embodiment, a membrane or device 10 having a sample receiving site 11 shown in this embodiment as a separate discrete pad. Downstream of the site 11 is a mobilization site 12 shown also as a separate pad and having thereon an appropriately labelled receptor to analyte 13 deposited in non-immobilized fashion so that it is capable of being moved or transported through the strip by flow of sample or other liquid.

Traps act to trap the analyte-bound labelled receptor. The trap may include a homogenous band as shown in FIG. 1 or a series of trap lines as shown in FIG. 2b. Alternatively, these lines can be placed close enough together so that the effect is that of a block of color or with spaces between them such that they appear as the rungs of a ladder. Alternatively, the space may be coated by spraying, thus providing a continuous line. The height to which the analyte bound labelled antibody migrates is proportional to the amount of analyte in the sample. To elaborate, visually this column could appear continuous or non-continuous, i.e. the bound labelled antibody might give a continuous height of color. Small traps for bound receptors of increasing avidity/affinity may be deposited as bands on the membrane for greater sensitivity. In this case, one band would be the lowest level of analyte, two bands a little more, etc.

For a reflectometer, the trap for bound receptor should function to evenly distribute the bound receptor that passes through the unbound receptor trap. This may be accomplished in any of a number of ways. For example, in one embodiment, the detection zone is impregnated with a low concentration of an anti-antibody or antibody binding protein such as protein A or G which functions to spread and capture the bound receptor.

In a preferred embodiment for reflectometry, the avidity/affinity of the trap for bound receptor particle is sufficiently low so that a single line is not formed. That is, the trap for bound receptor may include an anti-receptor having low affinity (e.g. $10^{-6}$M to $10^{-8}$M) for the bound receptor. This results in low binding so that interaction is dependent on the amount of particles in the mobile phase and time of contact.

In another embodiment, to enable spreading of bound receptor for enhanced visualization, the bound trap may be coated with a substance that acts like an ion exchange column and thus retards the flow of the bound. In some cases, i.e. with some membranes, failure to block the membrane or partial blocking will ensure that antibody which migrates onto it is bound to the membrane in a manner that permits a thermometer-like column to form.

Figure 4A:
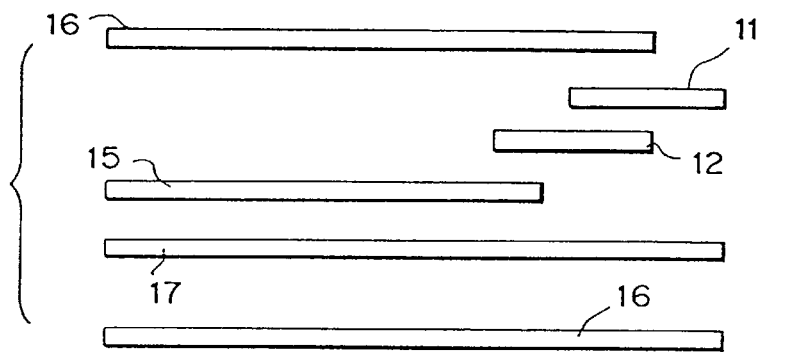
FIGS. 4a)–d) show exploded elevation views of various embodiments of the device of the invention.
Figure 4B:
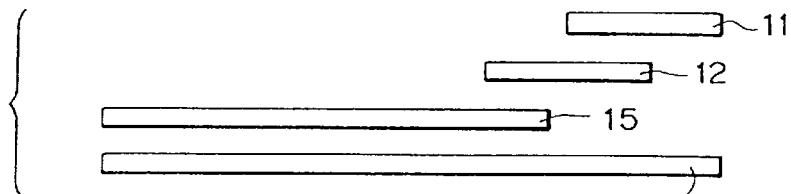
Figure 4C:
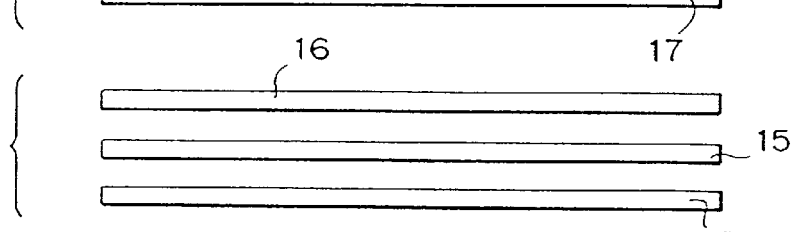
Figure 4D:
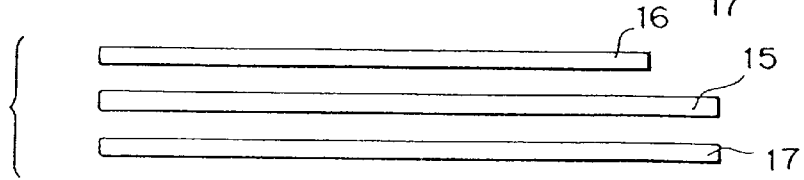

In the first embodiment, the receptor interacts with the analyte (protein, drug or hapten) in the sample in the mobilization zone. When the receptor and formed immune complexes (if any) reach the non-competitive reland trap, unbound receptor particles are stopped and bound receptor passes through to another detection zone 18 where it is trapped by interaction with a competitive ligand or an anti-receptor or a receptor for another free epitope or epitopes on the protein. Downstream of the labelled receptor mobilization zone 12 is the reland trap, zone 14, containing immobilized reland shown on membrane 15 as a dotted line block though this is usually invisible before use of the device. Optionally, but preferably, there are other detection zones such as 18, preferably immobilized, as noted above. While the device of FIG. 1 is shown as a composite of separate discrete zones or phases in liquid communication with each other so as to permit the flow of sample and reagents throughout the device, it may also be a unitary strip, that is a single layer strip of continuous unbroken membrane. (See FIGS. 4c and d.) In another embodiment, there is yet a further trap, for example, a receptor for the protein or receptor to provide more quantitative results.

The above composite is sandwiched between two laminating strips 16 and 17 which have adhesives on each surface contacting the membrane and which extend beyond the distal end of membrane 15 thereby to enclose the membrane at the distal end. Strip 16 may be foreshortened (see FIG. 4a) to expose an area on sample receiving means 11 for application of sample. If it is not, (see FIG. 4B), the proximal edge of 11 can act as the sample receiving site. In the preferred embodiment (not shown in FIG. 1), the lateral edges of the strip 16 and 17 extend beyond the lateral edges of the membrane 15 thereby completing the enclosure of the membrane within the laminated strips except at the sample application site. This enclosure technique defines a set volume of liquid volume capacity for the membrane and protects the membrane from contamination. The proximal end of the strip may have attached a wicking material for quickly absorbing and or filtering the fluid. This material may be attached by staple or laminating or glue or pressure. Thus modified the strip may be dipped in urine prior to being used in a reflectometer or it may be used in a urine stream, eliminating the need for a cup.

In use, sample is presented to the sample receiving site 11 from which it wicks, migrates or is transported by the chromatographic nature and/or capillarity of the membrane to and through the mobilization site 12. Assuming the sample is negative for analyte, there will be no reaction with the gold labelled antibody at 13 and the sample, together with the gold labelled antibody, will be transported from site 13 toward the trap 14. In the process, there will be a diminution of the reddish color imparted by the gold at the mobilization site as the gold-antibody conjugate moves away from its original site facilitated by the sample flow. As unreacted gold/antibody conjugate reaches the immobilized reland trap 14, it reacts with the reland trap in consequence of the selective properties of the latter. The reland trap is selected for its low affinity binding capability to the antibody or the receptor of the gold labelled complex and will bind thereto only in the absence of analyte. Thus, accumulation of color at the trap correlates with unbound receptor. Large excess of reland complex may be utilized to ensure that all unbound is captured at the reland trap zone. Reland trapping capacity may be increased by increasing valence, i.e., increasing the amount of reland on proteins or immobilizing reland proteins on latex. When purified ascites is used to prepare gold conjugates, it contains a certain percentage of non-relevant antibody, i.e., antibody that is polyclonal and is not reactive with the analyte. Generally this should be on the level of 10% of the total antibody. Presence of this antibody means that some gold particles contain a high proportion of non-relevant antibody and therefore will not be retained by the reland trap. These particles always show up in Trap for bound receptor, which is undesirable. For certain analytes, binding of analyte decreases the ability of the particle to bind to polyclonal anti-heavy and light chain. This property can be used to resolve the non-relevant antibody. A trap utilizing anti-heavy and light chain can be placed just distal to the reland trap. This trap then binds to particles which escape binding to the reland trap, not because they bound analyte but because they contain non-relevant antibody, which because it does not bind analyte it retains affinity for the anti-heavy and light chain traps.

If the sample is positive for analyte, an immune complex will form between the analyte and the gold-labelled receptor. Because of the characteristics of the reland trap, the trap 14 fails to bind the immune complex because it does not compete with the analyte for the receptor. Nor does it displace that analyte from the complex. Free analyte (if any) may release labelled receptor from the unbound trap. As a result, receptor/analyte complexed particles pass through the reland trap 14 as part of the labelled immune complex resulting in proportionately less color at the reland trap for unbound receptor. An intensity of color proportional to amount of analyte in the sample would then be displayed at a bound receptor trap 18 of the strip downstream of the reland trap 14 to indicate quantitatively or qualitatively the amount of analyte. The bound receptor trap 18 or detection zone may take the form of a laddered trap as described previously, although it is shown as a block 18 in FIG. 1. The trap may be immobilized as desired and be located at a desired portion of the strip.

In a preferred aspect, the immunodiagnostic strip is provided in the form of a laminated structure which enables or facilitates the quantitative or semiquantitative capabilities of the strip depending on the method of read-out used to indicate the amount of analyte present. The basic strip includes a membrane or porous strip impregnated with immunodiagnostic reagents and indicators. Any solid phase support either for laminating or simply for support can be used in the chromatographic embodiment, but plastic, mylar, and membranes, such as nitrocellulose or nylon, are preferred. It is preferred when laminated, that an adhesive be applied on each of the total inside surfaces of the two layers of anon-permeable, non-wettable material in such a way as to occlude the entire expanse of strip surface. At least one layer or one area of one layer of the laminating material should be capable of allowing visualization of the detection zone of the membrane. The laminated device may be sealed on the top, sides and bottom.

The lamination helps to ensure that the membrane is not exposed to contamination by the sample or by the environment except at an open or openable sample receiving area, ensures that sample interacts with membrane reagents rather than skating over or around them, and controls the speed of wicking which in turn controls the time of interaction. Steps can be taken to protect sample receiving area such as by providing an openable cover. Another advantage of lamination is that it prevents the passage of fluid across the top of the membrane or along the sides where it does not interact, (or interacts minimally) with the reagents. Lamination may preclude the use of reagent systems that require environmental oxygen, however. Alternatively, an air hole could be provided at the top of the strip to vent air, or air-permeable laminating materials may be used, but these may affect the quantitative nature of the device.

This form allows the device to be constructed in different configurations. For example, the strip may have a bound trap constructed of a read-out lines similar to a thermometer, the height of the color migration of analyte bound receptor of which is directly proportional to the amount of the analyte of interest in the sample. Alternatively, the strip may have a read-out which consists of two slightly separated blocks, block A, the reland trap which traps unbound receptor and block B, which binds analyte-bound receptor passing through the reland trap A as described in connection with FIG. 1. The strip is then read by visually comparing the two blocks or preferably by reading the reflectance in the two areas and expressing the reflectance as a ratio of, for example, unbound/bound, or bound/unbound, or bound/bound+unbound and comparing that ratio to results obtained from known concentrations, controls or standard curves. In a further embodiment, one could include a reading of the mobilization zone to correct for labelled receptor which may not have been mobilized.

These blocks may be used for a semiquantitative determination as well. For example, if only block A is colored, the sample is at level 0, if block A is darker than block B, the sample has level 1, if the two blocks are of equal color, the sample is at level 2, if block B is darker than block A, the sample is at level 3. If block A has no color and block B does, the sample is at level 4. If there is no color in either block, the test is not operative, thus providing an internal control.

As an alternative to the visual read, the blocks may be read in a reflectometer and the results reported as ratio of A:B or as ratio of A:A+B or B:A+B. In the above illustrations, Block A, the reland trap, serves to bind unbound antibody by trapping it in a non-competitive matrix, while Block B serves to trap the bound antibody by interacting it with a receptor which is highly specific for the bound receptor/analyte gold complex, i.e. a highly competitive ligand, or an anti-receptor antibody or a receptor for analyte. In a further embodiment, one could include a reading of the mobilization zone to correct for labelled receptor which may not have been mobilized.

In another preferred format, the unbound and bound traps are composed of a series of traps in the form of a thermometer/ladder such that the height of the color reached is proportional to the amount of analyte in the sample. In this format, the higher the amount of analyte present in sample, the higher the ladder rung reached.

When laminated as shown in FIG. 1, the device yields an assay which is quantitative because the amount of sample applied that can interact with the labelled receptor or antibody is controlled by the liquid capacity of the enclosed membrane without the requirement of an air hold. Since the strip is laminated over a determined distance, the membrane has a fluid capacity that is quantifiably controlled by the size and area of the membrane, the composite zones, if separate, the impregnation materials and the lamination process. Therefore, only a set amount of sample enters the strip to interact with the antibody. A key problem with other assay formats is that they require measurement of fluid for a quantitative assay.

Figure 5:
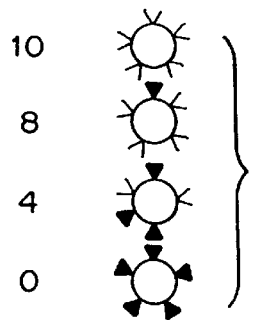
FIG. 5 is a schematic of a multi-trap device of the invention.

Another embodiment is depicted in FIG. 5. By the law of mass action one would expect that the number of Particles (P) bound to trap(T) or P+T=PT would be a function of the concentration of P and T. However, this is probably further complicated by the fact that the valence varies as described above. Thus if one envisions a series of high affinity traps arranged as a ladder, the first high affinity trap would trap those particles with the highest percentage of unbound antibodies. Therefore the particles arriving at second high affinity trap two would have lower valency and particle concentration would be decreased by the amount of particles left behind in trap 1. The lower valency of the particles passing through trap I must be compensated for by increasing the valency or affinity or both of affinity trap II to overcome the effect of lower concentration of P by increasing the concentration of T logarithmically. The concentration of T can be increased in two ways, 1 by increasing the valency of trap material as described below and 2 by logarithmically increasing the actual concentration of trap material immobilized on the membrane. One could increase the valency of high affinity ligand as follows. To increase the valence of a small ligand, one increases the amount of substitution of the ligand on the protein. It is well known that if one conjugates a small molecule to albumin then at a substitution of 1 to 2 molecules of drug/molecules of albumin there is lower affinity than at substitution of 10 to 11 molecules of drug/molecule of albumin. One can proceed in two ways to increase the valency of a protein analyte. If the epitope for which antibody is specific is known and there is available a high affinity peptide ligand one can increase substitution as described. If this is not possible one can immobilize the protein on a particle thus effectively multimerizing it. One can increase valency as above and further by absorbing the protein and ligand to latex.

An advantage of the high affinity ligand traps is that as the amount of analyte in sample increases a greater proportion of particles has lower valency and thus migrates higher on the ladder. This allows one to utilize less reagent for a visual response over a greater range.

A system of using a mobile multivalent receptor particle (any particle) has been developed where the binding or trapping of the particle is dependent on the affinity and valence of the mobile particle and the affinity and valency of the binding partner on the stationary phase. When valence is high there are many antibodies in the unbound state and the particles are retained chromatographically by very low affinity ligands such as the relands. When the valence is decreased by antibody sites being occupied by analyte, the affinity between trap and particles becomes insufficient to retain the particle. Thus, a higher affinity trap, i.e., one made by an increase in the valency of the trap material, an increase in the affinity of the ligand used to synthesize the trap material, or an increase in the absolute concentration of trap material, may be used to trap that particle.

The traps for bound antibody can be composed of high and very high affinity ligands for the antibody for example, immunogen which generally has affinity of 2 to 3 logs higher than the affinity of receptor/antibody for analyte.

When a series of identical avidity/affinity traps for bound particles is used, the signal at each successive ladder can become weaker and weaker, making it difficult to visually determine cut off. This situation can be corrected by increasing the concentration of high affinity ligands in the trap by two or three fold for each successive trap. This serves to produce successively distal traps with the same intensity of particles/label. While it is possible that these high affinity traps function by competing analyte off the receptor and allowing the particle to bind, the data does not support this and thus it is more probable they function because the particle contains some unbound antibody sites which interact with the high affinity ligand. An average of twenty antibody molecules/gold particle has been reported. Analyte in sample will distribute to these receptors on these particles by Poisson distribution, i.e., if there were enough analyte in sample to provide 10 analyte molecules to each particle then one would expect that there is a range of 0 to 40 analyte molecules bound per particle, with the median being ten. Particles having none or very low levels of analyte bound are retained in the reland trap. This is because retention in the reland trap requires that the particle have a critical number of unbound receptor sites or valence because the low affinity of reland trap. Binding of analyte essentially decreases the valence of the particle and thus decreases affinity for the reland trap. Therefore most particles not bound by the reland trap have free receptor sites, and these free receptor sites can interact with a high affinity ligand under the law of mass action. That is the chance of binding depends on the concentration of the reactants.

Receptors

In a preferred embodiment, the receptor is a monoclonal antibody to the analyte and labelled by binding to colloidal gold or other detectable particles. The receptor recognizes only one epitope and may be a monoclonal antibody to an immunogen or, theoretically, an affinity purified polyclonal antibody to a single protein epitope or a hapten. If more than one receptor to analyte is used, it would recognize a different epitope or the affinity for the trap would vary so that the trap would not function efficiently. The amount of antibody, usually an expensive component, is typically in the range of between about 0.5 and 1.0 μg/strip. Since this is an expensive reagent, it is important to keep the amount used low.

Other types of specific receptors can also be used. Examples include antigen-specific T-cell receptors, and ligand-specific ligands known to those skilled in the art.

Carriers

The receptor can be in solution or, more preferably, bound to a carrier such as a gold particle or latex bead. Most preferably, in a suspension when the carrier is a gold particle having bound thereto greater than two antibody molecules.

Labels

Suitable labels for use in this assay include, but are not limited to, colored or fluorescent dyes, chromagens, colloidal gold, enzymes, and latex. While the label may suitably be any label which by itself or through reaction with substrate may be visualized by eye or with instruments, major benefits are obtained when the label is non-enzymic. The receptor molecules can be bound to the particles as described in the examples or using other methods known to those skilled in the art.

Traps

Relands

Devices and methods for determining the presence and amount of an analyte in a sample through a binding reaction (or lack thereof) with a labelled receptor for analyte and removal of unbound receptor by use of a non-competitive trap for labelled unbound receptor (hereafter sometimes "unbound receptor") have been described. These are based on the discovery that a reland or "release ligand", will complex with a free receptor, that is, a receptor not bound to its binding partner, but will not complex with a labelled receptor/analyte immune complex (hereinafter sometimes "bound receptor"). The reland will not compete with the analyte of the receptor/analyte complex and is therefore a non-competitive ligand. The immune complex are stable, i.e., virtually irreversible in the presence of the non-competitive ligand. The reland is selected to have properties which are substantially different from the properties of ligands normally used in assays requiring ligand:receptor complexes. Relands are preferably provided in multimeric form to facilitate immobilization as a non-competitive ligand, although relands in monomeric form which can be immobilized are suitable as well. The formation of a suitable receptor:non-competitive ligand complex depends upon the characteristics of the reland. Other assays generally use competitive binding properties of ligands.

As noted by Butler in Chapter 17 of "Immunochemistry of Solid-Phase Immunoassay", "solution-phase, biomolecular noncovalent reactions are known to proceed according to the Law of Mass Action with similar forward rate constant ($k_1$) but with very different dissociation rates (Table 2) so that $k_2$ largely determines the equilibrium constant (Keq.; Equation 2)."

$$K_{eq.} = \frac{k_1}{k_2} \quad (2)$$

Table 2 at page 18 clearly shows that association constants are actually independent of dissociation rates. Butler shows the formula $$\frac{k_A \text{ Association Constant } [AbAg]}{k_d \text{ Dissociation Constant } [Ab_f] [Ag_f]} = K_A \text{ Affinity Constant} \quad (3)$$

indicating that the association and dissociation constants are not reciprocals of one another. Referring to Table 2 of Butler, it is clear there is no correlation between the association and dissociation constants. One observes that the correlation coefficient between the association and dissociation rates is less than 0.08; well below the value of at least 0.5 normally indicative of a correlation, and significantly different from the −1 value indicative of an inverse relationship.

Selection of Relands

In preparing a non-competitive ligand, the reland is generally selected from molecules structurally related to the analyte. An appropriate reland for a particular receptor to a target analyte will associate with the receptor only at high concentrations of reland when present as a monomer (lower concentrations may be used when the candidate is presented as a multimer) with slow kinetics and only in the absence of analyte. The reland does not detectably affect the essentially complete binding of analyte to the receptor nor does it bind substantially to the receptor in the presence of analyte. In one embodiment, the association rate constant of a monomeric reland and the receptor is less than or equal to about $10^5$ $M^{-1}$, preferably between $10^3$ $M^{-1}$ and $10^5$ $M^{-1}$, and most preferably around $10^4$ $M^{-1}$. When the reland is a multimer, for example a dimer, trimer or a higher -mer, or when conjugated to a carrier such a peptide (still a multimer as used herein), the association rate constant is dramatically increased. The larger molecular sizes tend to favor the formation over time of irreversible complexes with the receptor and may have higher cross-reactivity with the analyte. The irreversible nature of larger molecular complexes is generally due to factors other than immune interaction and so is non-specific in nature. However, despite this, the higher molecular weight multimers such as are obtained from bovine serum albumin ("BSA"), bovine gamma globulin ("BGG"), glucose-6-phosphate dehydrogenase ("G6PDH"), and others may produce suitable complexes in traps provided the cross-reactivity parameters are acceptable.

A reland may be an analog of the analyte, including an epitope of the analyte, a derivative of the analyte, a modified analyte, or an isomer of the analyte. Preferably, the reland differs structurally from analyte in a location or at or near the epitope. These differences may include chemical modifications, steric, configurational, conformational, or ionic changes. Preferably, ionic groups are substituted with a neutral polar groups, since ionic interactions are particularly strong, and may interfere with the assay.

Molecules prepared to structurally mimic the analyte are also analogs which may be used as relands. Such structural mimics may, but need not be, of the same chemical nature as the analyte so long as the epitope is chemically similar. Thus, for example, a peptide may be an analog of a protein. Once an analyte/receptor pair for investigation has been chosen, potential relands are selected from analogs of the analyte. Analogs of the analyte may be selected by identifying structures similar to analyte, selecting several with different portions of the molecule having been modified as taught herein and looking at cross-reactivity of such structure in a competitive assay for analytes as previously indicated. The modification may in some circumstances be only simple changes or substitutions in structure, such as one step dissociation or substitution of a single amino acid in a polypeptide chain. From those monomeric compounds with little or no competition for binding with the analyte to the receptor at $10^{-6}$ M concentration, several are selected to screen for their ability to provide a non-competitive trap.

If no analogs are commercially available, derivatives may be prepared by adding or deleting modifying groups to the analyte. Derivatives may also be natural metabolic products of the analyte. One of ordinary skill, having the information presented herein, will readily know how to prepare or identify derivatives of analytes for use in the invention. Changes in molecular structure of the analyte will alter the binding affinity of receptor for reland.

Modified analyte includes analyte conjugated with a steric interfering group. Addition of bulky groups, such as aliphatic, aromatic or cyclic molecules or sugars, or ionic groups, or preferably substitution of non-ionic groups for ionic groups, to an analyte or to a peptide can result in decreased binding affinity for receptor due to steric and/or charge interference. Alternatively, conjugation with a bulky group may cause a conformational change in the epitope of the reland that decreases binding affinity with the receptor. Chemical modifications of organic molecules are well-known in the art and may be used to modify reland. For example, cotinine can be modified by the presence of alkyl groups having up to 6 carbon atoms and most preferably, N-isopropyl or N-propyl groups to provide a preferred reland in an assay for cotinine.

Isomers of analytes are molecules with the same composition but different configuration. Typically, isomers will have a different configuration at a particular carbon center, e.g., cis versus trans, D versus L. Isomers include diastereomers, which have the opposite configuration at one or more chiral centers, and include enantiomers of analytes. Since biological binding interactions depend on configuration as well as conformation and composition, use of an isomer as reland can result in much lower binding affinity for receptors. Usually a decrease in affinity between isomers alone is not sufficient to create a reland, but an isomer may enhance the effect of other alterations.

Other types of reland molecules can also be utilized. For example, the difficulty in measuring bone alkaline phosphatase ("BAP") is that liver alkaline phosphatase ("LAP") in blood shares identical amino acid sequences, but varies in carbohydrate composition. This appears to alter the protein conformation and therefore the immunodeterminant profile slightly. It has been shown that only BAP binds to the lectin Wheat Germ Agglutinin ("WGA"). Therefore, the reland trap may be WGA which is known to bind BAP and not other AP's. Lectins have reland level affinities of a $10^{-3}$ to $10^{-4}$M. In this embodiment, the labelled receptor is a labelled (preferably gold labelled) antibody to AP. The antibody need not be specific to BAP since the WGA trap will serve to selectively separate the BAP from the other AP's. In this case the reland trap would bind the analyte of interact. Alternatively, the reland trap for unbound receptor can be a protein with low homology to alkaline phosphatase such as one of the alkaline phosphatase with an affinity for the BAP receptor of less than 1%, preferably less than 0.2%.

Where the analyte is a protein, the reland may be prepared by synthesizing peptide analogs of the epitope to which the receptor is specific. Recombinant DNA methods using site directed or other mutagenesis techniques to alter the amino acid sequence of the protein may also be used. These techniques are well-known to those skilled in the art (e.g., see Zoller and Smith, 1984, DNA 3:479–488; Oliphant et al., 1986, Gene 44:177; Hutchinson et al., 1986, Proc. Nat'l. Acad. Sci. U.S.A. 83:710).

Relands conjugated to suitable carriers can be screened for their ability to bind antibody by using a microtiter plate system. For example, to a reland/BSA conjugate coated on a plate, antibody is titered, added and incubated for one hour. Any binding would indicate that further evaluation was warranted.

To further evaluate the use of a reland conjugate, one can immobilize the conjugate as a trap on membranes in varying concentrations. The membrane is next blocked and laminated as described herein. The strip is then exposed downstream of the trap to labelled antibody and the ability of the trap to contain all the antibody as ascertained. Several factors are critical here in making the evaluation test.

1. The valence of the labelled antibody particle. If purified antibody is coated on gold sol, there are generally greater than 10 molecules of antibody/particle. The affinity of this material for the trap is higher than that of a monomer IgG and much higher than that of an antibody fragment such as a Fab.

2. The trap must be laminated to ensure that all receptor material interacts with trap material.

3. The affinity of the trap material may be affected by the immobilization and blocking steps and the resulting affinity can be higher or lower than predicted.

4. The affinity of the antibody on gold may be affected by immobilization and by an increase in valence. If the affinity is too high, one may dilute the analyte specific receptor with a non-relevant receptor or other protein thereby decreasing valence and affinity.

Linking Groups

The trap material may also include a linking group which may be used to conjugate the reland (or other trapping agent) to a carrier. Linking groups may be selected from bifunctional cross-linking agents to facilitate attachment of carrier to the reland where the functional groups of the reland and the carrier do not admit of direct attachment. An example of a linking group is aminocaproic acid. Also, bulky linking groups may be used to sterically hinder binding of reland trap to receptor. An example of a bulky linking group is p-aminobenzoic acid. Both linking groups and labels can decrease or increase the association and/or dissociation constant. Therefore, selection of a reland as a trapping material requires evaluation of the reland multimer including linking groups and carriers.

Quantitation of Reland

A suitable reland trap material must be sufficient to trap virtually all labelled receptor. Typically, there will be at least a five-fold molar excess over the amount of receptor sites. Further, increasing the trap material 10% over the minimum needed to trap all labelled receptor should not substantially affect the ability of analyte-bound labelled receptor to pass through the trap zone without being trapped.

Preferably, at least twice the minimum amount of reland trap needed is used to protect against variation in receptor concentrations and changes due to environmental causes.

Competitive assays useful for evaluating potential relands can be run in an ELISA format, but any competitive assay technique may be used. For example, a reland is much less effective than analyte for inhibiting binding of receptor to analyte on a solid phase. A molecule that is a poor competitive inhibitor relative to analyte can be a good choice for use as a reland.

A low concentration of a suitable reland may actually appear to enhance binding of receptor to analyte in a competitive assay. Thus in a competition type assay increased absolute signal in the presence of a lower concentrations of the reland candidate may be a suitable reland.

When a direct assay is used to evaluate a potential reland, binding of receptor and reland is compared to binding of receptor and analyte. An ELISA format is well-suited for this type of assay, but other assay formats can also be used. Typically, in an ELISA test, binding activity is represented by titer, i.e., dilution or concentration of receptor with a particular binding activity. Alternatively, specific activity at the same receptor concentration can be compared.

The microtiter plate method of evaluating a reland takes advantage of the ability of multimer reland structures to exhibit increased association constant. When the microtiter plate is coated with a potential reland candidate conjugated to protein, the complementary labelled antibody is added and a complex allowed to form. If the reland is suitable, release of the labelled antibody from the complex will occur and can be detected in a sample supernatant after sample containing analyte is added. A microtiter plate format is used for screening for potential relands because of its ease. To quickly and easily screen potential relands, microtiter plates are pre-coated with albumin at a concentration of 2 $\mu$g/ml. The various reland candidates bearing —COOH or —$NH_2$ groups are added with carbodiimide to the wells and allowed to interact with the albumin overnight. After washing, the reland-coated plate can be tested, first to evaluate its ability to bind antibody, and then for its ability to release. It is possible in this format to screen dozens of reland candidates quickly and simply in a day or so.

A non-competitive ligand for a receptor for human albumin could be a) albumin from another species with low cross-reactivity but sharing structural features, or b) human albumin treated in such a manner as to drastically change its affinity for the receptor.

Such changes are known in the art and have been produced by means which cause partial or complete denaturation such as some immobilization procedures, acid or organic treatments, heat treatments, salt treatments, etc.

As an aid in visualizing the bound analyte which passes through the reland trap, other traps may be employed to provide additional detection zones. The amount of color at these other detection zones downstream of the unbound trap are an indication of the presence and quantity of analyte in the sample.

Between the unbound trap and the labelled receptor, there may be provided a time delay reagent such as a relatively slowly dissolving impregnation line to provide sufficient time for the formation of the immune complex or merely an expanded distance for time delay purposes.

Included among the benefits of a reland trap are those of cost and quality control. Since reland trap materials can be synthesized from short peptides and other small molecules, they can be made at a fraction of the cost of some other reagents.

The trap for bound can be designed to bind particles having lowered valences, i.e., having several to many sites on a particle bound to analyte. In the simplest form, the "trap" includes unbound immobilized analyte, which binds to the unbound receptor sites on the particles, thereby trapping the particles.

Competitive Ligand Trap

A competitive ligand can be used as a trap. A competitive ligand has an approximately equal affinity for ligand as for analyte.

Immunogen Affinity Trap

A trap designed to bind particles having even a greater number of bound receptors can consist of immobilized immunogen.

Anti-Receptor Trap

Anti-receptor traps are designed to bind all particles, irregardless of their valence, whether completely occupied with analyte bound to receptors or otherwise. In the preferred embodiment, the anti-receptor is an antibody reactive with an epitope not obscured by binding with analyte, for example, an anti-IgG antibody, or an antibody prepared to the receptor particle based on mobile phase.

Application of Sample

The sample may be applied to the strip in a variety of ways. For example, the proximal end of the strip may have exposed a part of the strip to act as a sample application zone capable of absorbing sample (intrinsically or by virtue of being impregnated with a hydrophilic substance) and allowing it to wick distally towards the mobilization zone. The exposed portion may be introduced to the sample by submerging this portion of the strip into a container of the fluid or by holding the strip into a stream of fluid to moisten it. Alternatively, a drop of fluid may be placed on the membrane. The proximal end of the strip may have attached a wicking material for quickly absorbing and or filtering the fluid. This material may be attached by staple, laminating, glue or pressure. The modified strip may be dipped in urine prior to being used in a reflectometer or it may be used in a urine stream, eliminating the need for a cup.

The sample application zone may be a portion of the diagnostic membrane, it may be a membrane selected to ensure maximum remobilization of labelled reagent, it may be a pad overlapping the mobilization zone, or it may be a prefiltering pad covering the sample receiving area of the mobilization zone. The prefiltering pad could be a membrane or material with controlled pore size to prevent blood cells and debris from the sample from entering the diagnostic reagent impregnated areas of the membrane or it could function to buffer and remove debris such as might be required with certain urine, saliva or vaginal samples or with some environmental samples. If the strip is to be used by submerging in liquid for the duration of the assay, it may not be necessary to provide a pre-membrane absorbent pad for the purpose of holding sample until the membrane has time to absorb sample.

The distal end of the membrane may be impregnated with a pH indicator chromogen such that color is observed when it is moistened indicating that a quantitative amount of fluid has traversed the length of the strip. Alternatively, the distal end could be impregnated with a desiccant indicator such as $CaSO_4$ which is blue when dry and pink when wet. This indicator will turn color if the strip is moistened by sample or if the strip has been inadvertently exposed to environmental moisture. Therefore, a pink color could indicate a complete test or that a test strip could not be used.

Embodiments of the Devices

Diagnostic Strips

Figure 2:
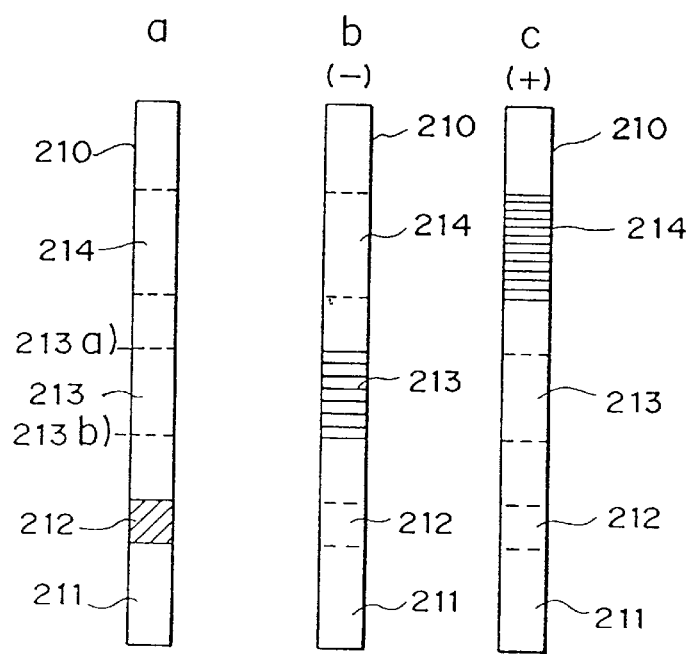
FIGS. 2a–2c and 3a–3c depict different embodiments of the device a) before use and after use with b) a negative sample, and c) a positive sample.
Figure 3:
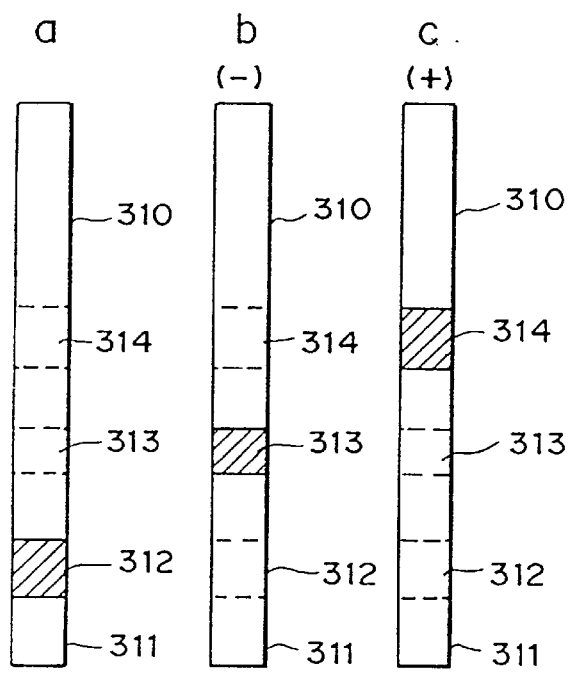

Reference will now be made to the drawings, FIGS. 2 through 4, which depict differing embodiments of the device. Each of FIGS. 2 and 3 shows a strip in unused form followed by a strip exposed to a negative sample and a third strip exposed to a positive sample. The strips are laminated, but the laminating layers are not shown. The construction of the strip is shown in FIG. 1.

Referring now to FIGS. 2a–c and FIGS. 3a–c, specifically FIG. 2a and FIG. 3a, there is shown therein a chromatographic strip or membrane designated as 210 and 310, respectively. The strip has a sample receiving site 211 and 311, respectively, provided at one end of the strip. Downstream of the sample receiving site is the mobilization zone 212 and 312, respectively, containing the labelled receptor. In the particular discussion herein, a colloidal gold-labelled antibody to the analyte is used in the mobilization zone. The gold/antibody complex is impregnated in the strip so that it can be moved along the strip by the force of the liquid sample moving through the chromatographic strip or by wash fluids and the like if they are applied. The reland trap in FIGS. 2a–c is at 213 and in an unused strip would be invisible to the naked eye since it is impregnated in the strip from solution and has no color of its own unless one is otherwise provided. For ease of reference, the reland trap zone 213 is shown as being between two dotted lines at the outer reaches of 213 which are designated as 213a and 213b. The reland trap in this particular embodiment is impregnated in the form of discrete lines so as to resemble a ladder although that would not necessarily be apparent from visualizing the unused strip. The strip in FIGS. 2a–c and FIGS 3a–c also contains an immobilized bound trap 214 and 314, respectively, in the form of a ladder shown in FIG. 2c, (though this would be invisible in FIG. 2a).

In use and referring now to FIG. 2b, a sample negative for analyte is applied to site 211. It thereafter moves along the strip 210 until it meets the gold-labelled receptor at 212 at which point it mobilizes the gold-receptor and moves it along the chromatographic medium. This diminishes the color at the mobilization zone 212 FIG. 2b. Since the sample is negative for analyte, there ideally will be no reaction with the antibody of the gold-antibody complex and the entire complex should therefore be captured by the reland trap at 213 yielding a series of stripes or rungs of the ladder. The reland is used in large excess to the receptor to ensure that visually all of the gold-labelled receptor is captured by the reland.

Referring now to FIG. 2c, when a positive sample is applied at the sample site 211 of FIG. 2c, the sample together with the gold-labelled antibody migrates through the chromatographic strip, and because of the presence of the analyte, will form a gold-labelled antibody-analyte complex on the particle. The complex will not be trapped by the reland trap at 213, and will proceed instead to the bound trap 214 where the color provided by the gold colors the strips of the traps in proportion to the amount of analyte in sample. The intensity and the height of the color will be a semi-quantitative indicator of the amount of analyte in the sample.

FIG. 3 represents another embodiment where the reland trap instead of being in the form of a series of lines or rungs shown at 213 of FIG. 2, is actually in the form of a block of reagents designated in FIG. 3a by the dotted lines bounding 313. A negative sample shown in FIG. 3b would cause the trap to capture the unbound antibody gold complex and yield the color at 313 whereas in FIG. 3c, if the sample were positive, the gold labelled complex of analyte/antibody would pass through the reland trap at 313 and accumulate downstream at 314 to indicate a positive result.

BioSensors

Another format which can be used is that of a biosensor. In this case, trap for unbound receptor prevents labelled unbound receptor (the label including gold or other conducting or conductance modifying substance) from reaching an electrode coated with a material which traps bound labelled receptor. This acts as the trap (or detection zone when connected to a resistance measuring circuit) for bound receptor with the change in resistance or current being proportional to the amount of analyte in sample. The unbound trap need not be a membrane, but may include a gel or phase which limits diffusion and, therefore, selectively prevents diffusion of unbound to the electrode where the bound accumulates because of the bound trap.

When analyte comes in contact with labelled receptor, two species of receptor result, bound and unbound. The unbound receptor is trapped in the trap for unbound receptor. The trap for unbound receptor is in the matrix surrounding the electrodes and it prevents diffusion of unbound to the test electrodes. The bound antibody passes through the trap to the detection zone. In this form, using electron modulator or label, the antibody may be labelled with an electron flow enhancer such as ferrocene or an electron sink such as a molecule or enzyme that absorbs electrons such as catalase. The first electrode may constitute the reference electrode and may include, for example, an electron generating enzyme system such as glucose oxidase. The trap for bound receptor may include a molecule as previously described that functions to trap the bound receptor and which is situated in close proximity to an electrode-proximal electron generating enzyme system to enhance or inhibit electron flow.

In a preferred biosensor embodiment, the receptor is labelled with multiple copies of the label modulator so that many copies of the modulator are delivered for each enzyme molecule for electron flow. When the enzyme is glucose oxidase, the receptor could be labelled with ferrocene. In this case, when antibody binds near or at the glucose oxidase, it supplies ferrocene which enhances transfer of electrons from glucose oxidase to the electrode. Alternatively, the antibody could be labelled with catalase in which case binding near or at glucose oxidase would inhibit the electrons from reaching the electrode. It should be understood that one electrode would serve as a reference electrode to control for noise and the other electrode would trap bound antibody.

In a decreasing resistance embodiment, the antibody is labelled with gold or silver or other conductor. The electrode is thin and has high resistance. Binding of the gold or silver labelled antibody to the bound trap electrode (probably gold or silver) decreases the resistance. Unbound antibody is trapped in the gel which contains the trap for unbound. Bound antibody is free to diffuse and become trapped at the bound electrode where it increases signal. In another embodiment, the electrode could be gated by the bound trap such that conductance across the gate is facilitated by conducing receptor label complex binding at the gate.

As can be seen, there are a variety of configurations that may be employed which will be apparent to one skilled in the art. These will be more readily apparent from the following examples of specific embodiments of the invention.

EXAMPLE 1

Gold-Anti-cotinine Antibody Conjugate Preparation

Colloidal gold, made by Serex (Maywood, N.J.) according to Roth in Techniques in Immunocytochemistry, vol 1, p. 110 ed by Bullock, G. and Petrusz, P., Academic Press, Inc. 1982. was conjugated to affinity purified rabbit anti cotinine antibody (commercially available under the name of polyclonal rabbit antisera to cotinine from Serex) according to the conjugation procedure described by Roth J., as follows:

100 $\mu$g of affinity purified antibody was mixed with 10 ml of 0.01% colloidal gold at 2.5 mM borate buffer, pH 9.0. After 1 hour reaction, bovine serum albumin was added to a final concentration of 0.1%, and the preparation was concentrated about 10 times with centrifugal concentrators Microsep, from Filtron (Northborough, Mass.).

Finally, the gold preparation was spun down for 15 minutes at 6,000 RPM. Supernatant with unabsorbed antibody was discarded and the particles were resuspended in I ml of diluent consisting of 0.025 M Tris/HCl Buffer, pH 8.2, 0.1% bovine serum albumin. and 0.05% sodium azide.

100 $\mu$l of gold-anti cotinine antibody conjugate working solution was measured with a microtiter plate reader, S.L.T.340ATC. O.D. at 550 nm was 1.732.

EXAMPLE 2

Gold-Anti-theophylline Antibody Conjugate Preparation

Colloidal gold of particle size 20 mm from Zymed Lab, Inc. (San Francisco, Calif.) was conjugated first to goat anti-mouse IgG, Fc antibody from Jackson Immuno Research Lab, Inc. (West Grove, Pa.) according to procedure described by Roth J in Techniques in Immunocytochemistry, vol 2, p. 230 ed by Bullock, G. and Petrusz, P., Academic Press, Inc. 1982. 100 $\mu$g of purified antibody was conjugated to 10 ml of 0.01% colloidal gold in 2.5 mM borate buffer, pH 9.0. After blocking by bringing to 0.1% bovine serum albumin, the preparation was concentrated to 1 ml volume. See Example 1.

0.5 ml of concentrated gold-anti-mouse IgG, Fc conjugate was interacted with 0.5 ml of anti-theophylline Mab from Biodesign (Kennebunk, Me.) at a concentration of 0.09 mg/ml in a buffer consisting of 0.025 M Tris/HCl buffer, pH 8.2, 0.1% bovine serum albumin, and 0.05% sodium azide. After 1 hour of interaction at RT, the gold particles were spun down; supernatant with unbound antibody was discarded and the particles were resuspended in 0.5 ml of diluent consisting of 0.025 M Tris HCl, buffer pH 8.2, 0.1% bovine serum albumin, and 0.05% sodium azide. 100 $\mu$l of final preparation of gold conjugate was placed in a microtiter plate well and O.D. at 550 nm was read. The working solution of gold conjugate had an O.D. of 2.084 at 5–50 nm.

EXAMPLE 3

General Procedures for Preparing Nylon Membranes

In each of the examples which follow, the nylon membrane was obtained from Pall Corp. (East Hill, N.Y.). The product is designated BIODYNE™. The membrane is provided as a piece approximately 8 cm by 18 cm, although any size can be used and indeed in the preferred manufacturing process rolls would be used. The location and the size of the various reagents coated on the membrane will be a function of the size of the ultimate strips, the volume of the product to be used, the width and length of the strip and the configuration decided for the particular analyte being detected.

In general, however, the trap for the unbound receptor is generally formed as a 2–3 mm wide band parallel to the length direction of the membrane. The coated membrane is allowed to dry in air or the oven and then the trap for the bound material is applied in whatever configuration is desired for purposes of the test. For example, it could be supplied in ladder form or in a block form. The distance between the first trap and second trap is, of course, a function of the kinetics of the ultimate strip and the reagents and analytes sought to be protected. After the deposition of the bound and unbound traps in whatever configuration is desired, a blocking agent is applied to the membrane to prevent non-specific binding. Typically, any blocking agents that are normally used in the immunoassay art can be employed.

After each step, the treated membrane is dried so that each subsequent step is performed on a dry membrane. In the preferred embodiments, after the prepared membrane has had the first and second traps deposited and has been blocked, it is then placed onto a mylar strip which is at least coextensive with the membrane itself and has an extended portion which is not occluded by the membrane itself. The proximal extended portion is provided to act as a mylar support area for the gold mobilization zone and sample application zone which are placed sequentially in fluid communication with the membrane itself. A distal extended area may be provided to seal the membrane at the distal end. Thereafter, when desired, a final mylar or other laminating layer is applied with adhesive to the non-occluded side of the strip to form a sealed laminated device having at least a portion open to receive sample. Individual strips may then be cut from the large composite membrane.

EXAMPLE 4

Cotinine Dipstick—Two Bands Format

A. Using the procedure in Example 3 for making the nylon membrane supported on mylar strips, a large piece of nylon membrane Biodyne A, 5 μm pore size, was cut into a rectangular piece 8 cm by 18 cm. Using a instrument obtained from Camag Corporation, Wilmington, N.C. 28401, and applying by airbrush, a first trap, i.e. a trap for the unbound material, was laid down on the membrane strip in the form of a band 3 mm wide approximately 2.5 cm from the bottom of the membrane. 120 μl of the coating solution was used to make the band. The trap material was the reland propylcarboxy norcotinine conjugated to bovine gamma globulin at a concentration of 2 mg/ml in 0.05 M-phosphate buffer at pH 7.5.

The second trap, that is the upper trap or the trap for bound material, was laid down in the form of a 3 mm wide band 2 mm distal to the first trap. The coating solution for this second trap was goat anti-rabbit IgG, Fe antibody from O.E.M. Concepts, Inc. (Toms River, N.J.) used at a concentration of 0.25 mg/ml in 0.05 M phosphate buffer pH 7.5. After each deposition of the trap, the membrane was dried for several hours at room temperature and then soaked for 30 minutes in a blocking buffer consisting of 0.05 M Tris/HCl, pH 8.0. 0.5% casein, 5% sucrose, 0.1% TWEEN™ 20, 2 mM magnesium chloride, 0.15 M sodium chloride, and 0.1% sodium azide.

After the blocking solution was applied, the strip was dried overnight at room temperature with final drying being accomplished in a vacuum chamber at room temperature for more than 1 hour.

The strip was then laminated between two plastic supports in the following way. A strip of plastic designated Arcare 8259 from Adhesive Research, Inc. (Glen Rock, Pa.) was applied to the backside of the prepared membrane leaving, an exposed portion to act as a receiving area for the mobilization zone. A mobilization zone including a piece of polyester membrane carrying gold particles conjugated to anti-cotinine antibody prepared as described in Example 1 was used. 160 microliters of gold conjugate was applied along 16 cm of the polyester piece. The mobilization zone was then placed at the bottom of the nylon membrane overlapping it by 3 mm. The plastic adhesive backing had been totally coated with an adhesive so that all of the polyester membrane would adhere to the backing strip.

Thereafter, an application zone was applied to the thus prepared membrane by applying a piece of either filter paper or polyester over the mobilization zone overlapping it by 5 mm, but leaving the gold particles exposed. The entire assembly was then top laminated with Arcare 7843, also from Adhesive Research, Inc. (Glen Rock, Pa.) which uses the same adhesive, but a different mylar thickness. The top lamination was applied leaving some area of the application zone uncovered. Depending on preferences and the assay, the entire membrane assembly including the application zone and the mobilization zone can be covered leaving only the edge of the device open or available for applying sample to the device or in some cases dipping the strip into the sample.

After the entire laminated assembly was prepared, it was cut into individual strips 4 mm wide. When a hot knife is used to cut the laminated membrane into strips, the heat will tend to seal all of the edges coming in contact with the knife scaling the sides of the membrane within the plastic layers used as the laminating materials. Then only that portion at the application area which is left open may either be dipped into a sample at its edge or may have sample applied to it. If desired, the cutting into strips can be done without sealing the edges. In the preferred mode of operation, the membrane is cut and placed on the mylar in such a manner as to provide adhesive on all sides of the membrane and, in this case, the mylar can serve as the packaging of the strip.

Assay Run

Individual dipsticks were placed into small test tubes or cups containing urine cotinine controls or urine samples with different cotinine levels.

Sample absorbed by the application zone wetted the mobilization zone and mobilized the gold particles which migrated with sample flow through the nylon membrane to the top of the strip.

Visual Test Results

For the cotinine negative sample most of the color was at the lower trap of the strip and only a minimal amount of color was at the upper trap site. Not all rabbit polyclonal anti-cotinine reacts with the lower trap.

For the cotinine control at 100 ng/ml and higher, the color at the upper trap was darker than at the lower trap.

With increasing cotinine levels, the color of the upper trap of the strips appears gradually darker but the color of the lower traps appears lighter. For high cotinine levels, e.g. 5,000 μg/ml, there is a very strong color at the upper trap and no color or only a minimal amount of color at the lower trap site of the strip.

Measurement of Test Results

Color density at each trap site was measured by Gretag D19C Remission Densitometer (Switzerland). Results are summarized below in Table 1.

TABLE 1

Results obtained from Cotinine Dipstick.

| COTININE LEVEL (ng/mL) | UPPER BAND *– | LOWER BAND* – | RATIO (U/L) | RATIO U/TOTAL (U+L) |
|---|---|---|---|---|
| 0 | 0.070 | 0.180 | 0.39 | 0.28 |
| 50 | 0.073 | 0.083 | 0.88 | 0.47 |
| 100 | 0.097 | 0.097 | 1.00 | 0.50 |
| 200 | 0.080 | 0.060 | 1.33 | 0.57 |
| 500 | 0.090 | 0.040 | 2.25 | 0.69 |
| 1000 | 0.100 | 0.020 | 5.00 | 0.83 |
| 5000 | 0.105 | 0.000 | >10 | 1.00 |

*The values are the mean of three readings.

Visually one can distinguish 5 different levels in a two band system (Rating 1 is nearly impossible to achieve with a polyclonal, as one reland can only trap 1 antibody specifically.) These are:

| Lower | no Upper | 1 |
|---|---|---|
| Lower > | Upper | 2 |
| Lower = | Upper | 3 |
| Lower < | Upper | 4 |
| no Lower | Upper | 5 |

The actual cut off or sensitivity of the assay is affected by the amount of antibody on the gold and/or the epitope density on the trap, as seen in Example 7. That is, to increase sensitivity, one decreases the amount of antibody or valence of a gold particle which decreases affinity. This Example was designed for a 100 ng/ml cut off for which a visual signal was Upper Band=Lower Band. The above procedure was used to produce cotinine dipsticks and tested as shown below.

Forty nine urines were analyzed for cotinine levels by dipstick. Cotinine values from an Elisa assay were known. A sample was classified as negative if the lower band was clearly darker than or equal to the upper and positive if the upper band was darker than the lower. The results are shown below in Table 2.

TABLE 2

| | Cotinine (ng/ml) | | |
|---|---|---|---|
| | <50 | 60–100 | >100 |
| + | | 1 | 27 |
| – | 19 | 2 | 0 |

All samples with less than 100 ng/ml were negative. All samples greater than 100 ng/ml read positive. Of the three samples read between 60 and 100 ng/ml, one read positive and two read negative.

B. Variation of Two Bands Format with the same non-competitive lower trap and a competitive upper trap.

For the lower trap, propylcarboxy norcotinine-bovine gama globulin conjugate at a concentration 2 mg/ml of 0.05 M phosphate buffer, pH 7.5 was coated in a form of 8 mm wide band. 200 µl of the above solution was used to coat a band, 8 cm long.

For the upper trap, 200 µl of carboxycotinine-bovine gamma globulin conjugate at a concentration 1 mg/ml of 0.05 M phosphate buffer, pH 7.5 was coated in an 8 mm wide band.

Coated nylon membrane was processed and assembled the same way as in Example 3.

Dipsticks were run in urine cotinine controls with different cotinine levels and after development color densities of both traps were read with Gretag densitometer. Results are in Table 3 below.

TABLE 3

Results obtained with Cotinine Dipstick

| COTININE LEVEL (ng/mL) | UPPER BAND*– | LOWER BAND*– | RATIO U/L | RATIO U/TOTAL |
|---|---|---|---|---|
| 0 | 0.03 | 0.118 | 0.25 | 0.20 |
| 100 | 0.04 | 0.07 | 0.57 | 0.36 |
| 500 | 0.05 | 0.03 | 1.67 | 0.62 |
| 5000 | 0.06 | 0.017 | 3.59 | 0.78 |

*The values are the mean of three readings.

This test was optimized for 200 ng/ml cutoff, i.e. at 200 ng/ml at which concentrations the upper trap was of the same intensity as the lower trap.

EXAMPLE 4

Three Bands Format

A nylon membrane, BIODYNE™, 5 µm from Pall Corp. (East Hill, N.Y.) was cut into a piece 8 cm×10 cm.

Each of three traps was coated by CAMAG instrument in the form of 3 mm wide bands separated with 3 mm distance between each other. 50 µl of each coating solution was needed to make each 8 cm long band.

The first trap, i.e. for unbound, was prepared as follows: a solution of propylcarboxy norcotinine-bovine gamma globulin conjugate at 2 mg/ml of 0.05 M phosphate buffer, pH 7.5, was coated along the nylon membrane at 2.5 cm distance from the bottom of the membrane.

The middle trap, i.e. for bound receptor, was carboxycotinine-bovine gamma globulin conjugate, with affinity for a competitive binding partner, coated at a concentration of 1 mg/ml in the same phosphate buffer.

The upper trap was goat anti-rabbit IgG, Fe Antibody from O.E.M. Concepts, Inc. (Toms River, N.J.) coated at concentration of 0.25 mg/ml of the same phosphate buffer. The coated membrane was dried, blocked, dried again, assembled and laminated the same way as the membrane in Example 3. The laminated, assembled membrane was cut into individual strips, 3 mm wide.

Assay Run

150 µl of urine cotinine control at different cotinine levels was applied on the application zone of each dipstick. Sample absorbed by the filter paper pad of the application zone, wetted the mobilization zone and mobilized the gold particles which migrated with sample flow through the nylon membrane to the top of the strip.

Visual Test Results

For the cotinine negative sample, the lowest trap showed the darkest color. The middle trap showed less color and the upper trap was the lightest.

For the cotinine control at 100 µg/ml, all three traps showed color of almost the same intensity. For the cotinine control at 500 µg/ml, the upper trap was the darkest and the lower trap was the lightest. At a cotinine level of 5,000

μg/ml, only the middle and upper traps were visible; the upper was the darkest.

Measurement of Test Results

Color density at each trap site was measured by Gretag D19C Remission Densitometer (Switzerland). Results are summarized in Table 4.

TABLE 4

Cotinine Levels obtained using Multi-trap Dipstick Assay

| COTININE LEVEL (ng/mL) | UPPER TRAP* (U) | MIDDLE TRAP* (M) | LOWER TRAP* (L) | RATIO U/L |
|---|---|---|---|---|
| 0 | 0.04 | 0.08 | 0.15 | 0.27 |
| 100 | 0.07 | 0.07 | 006 | 1.12 |
| 500 | 0.12 | 0.09 | 0.04 | 3.0 |
| 5000 | 0.14 | 0.07 | 0.01 | 14.0 |

*The values are the mean of three readings.

This test was optimized for cut off of 100 ng/ml. The use of three traps allows a greater range of non-instrument based interpretation.

| TRAP 1 | TRAP 2 | TRAP 3 | LEVEL |
|---|---|---|---|
| Lower | — | — | 1 |
| Lower > | Upper 1 > | — | 2 |
| Lower = | Upper 1 > | Upper 2 | 3 |
| Lower = | Upper 1 = | Upper 2 | 4 |
| Lower < | Upper 1 = | Upper 2 | 5 |
| Lower < | Upper 1 < | Upper 2 | 6 |
| — | Upper 1 < | Upper 2 | 7 |

The above levels can be correlated to standard concentrations of cotinine by the user.

EXAMPLE 6

Band/Ladder Format—Cotinine

A nylon membrane, BIODYNE™, 5 μm from Pall Corp. (East Hill, N.Y.) was cut into pieces 8 cm×10 cm.

The first trap (lower trap) was coated in the form of 4 mm wide band along the nylon membrane at 2 cm distance from the bottom of the membrane. 80 μl of cotinine reland, propylcarboxy cotinine-bovine gamma globulin conjugate at a concentration 2 mg/ml of 0.05 M phosphate buffer, pH 7.5 was used as the band.

The second trap (upper trap) was coated in the form of 10×1 mm thin lines in 1 mm distance from each other. The upper trap was placed at 6 mm above the first trap. Each of 10 lines was made by depositing a 10 μl solution of carboxy-cotinine-bovine gamma globulin conjugate at concentration 1 mg/ml of the same phosphate buffer.

After coating, the membrane was dried, blocked, dried again, laminated, and assembled as in Example 3.

Individual dipsticks were cut 3 mm wide, and run with different level cotinine controls. Strips run with cotinine negative sample showed the lower trap with strong color and at the upper trap only the first bottom band of a ladder was strong while the next four were weak.

With increasing cotinine levels in the samples, the lower trap became increasingly visible and at the upper trap, the ladder bands became more visible and stronger in color.

Strips run with higher cotinine levels showed almost no lower trap color with all 10 ladder rungs being strong in color.

| COTININE LEVEL ng/ml | LOWER TRAP COLOR DENSITY | UPPER TRAP AMOUNT OF VISIBLE LADDER BANDS AND COLOR DENSITY |
|---|---|---|
| 0 | 0.185 | First bottom band strong, 4 next weak |
| 100 | 0.14 | 3 bottom stronger, 3 next weak |
| 500 | 0.07 | 8 bands visible |
| 5000 | 0.02 | 10 bands visible |

EXAMPLE 7

Increasing the Sensitivity of the Cotinine Assay

To increase the sensitivity of the cotinine assay the valence of the receptor particles was decreased relative to the amount of antibody by diluting the amount of anti-cotinine used for coating the gold sol particles by 20% with Chicken IgG (Sigma). Dilutions of more than this decreased the affinity of the gold labelled particles to the extent that unbound was not efficiently trapped by the reland trap. All strip preparation procedures are as in Example 3. Strips were tested against the following concentrations of cotinine as sample and the amounts of bound and unbound material measured by densitometer at each trap. The resulting tests showed a ten-fold increase in sensitivity over the undiluted antibody.

TABLE 5

| | COTININE CONCENTRATION ng/nl | | | | | |
|---|---|---|---|---|---|---|
| | 0 | 10 | 25 | 50 | 100 | 500 |
| Bound Trap | .09 | .08 | .09 | .09 | .09 | .10 |
| Unbound Trap | .07 | .045 | .03 | .02 | .01 | .01 |
| Ratio Bound/Unbound | 1.29 | 1.77 | 3.0 | 4.5 | 9.0 | 10.0 |
| Ratio Bound/Total | .56 | .64 | .75 | .81 | .90 | .91 |

In the absence of analyte, about 50% of polyclonal anti-cotinine is stopped by the reland trap. The variety of affinities in a polyclonal antisera make it very difficult to trap all of a polyclonal antibody with one reland epitope.

EXAMPLE 8

Two Bands Format for Theophylline Dipsticks

A. Nylon membrane, BIODYNE™, 5 μm from Pall Corp. (East Hill, N.Y.) was cut into pieces 8 cm×10 cm.

First trap (lower) was coated in the form of an 8 mm wide band along the nylon membrane at 1 cm distance from the bottom of the membrane. 200 μl of coating solution was used to make the band 8 cm long. Coating was done by CAMAG instrument. As a first trap, reland, theophylline-7-acetate-bovine gamma globulin conjugate was used at concentration 2 mg/ml in 0.05 M phosphate buffer, pH 7.5.

Second trap (upper) was coated also in the form of an 8 mm wide band along the nylon membrane at 2 mm distance above the first trap. 200 μl of coating solution was used to make the band 8 cm long. As a second trap, goat anti-mouse IgG, whole molecule (from Jackson, West Grove, Pa.) at concentration 0.25 mg/ml in 0.05 M phosphate buffer, pH 7.5 was used.

After coating and drying a few hours at room temperature, the membrane was soaked for 30 minutes in blocking buffer, consisting of 0.05 M Tris/HCl, pH 8.0, 0.5% casein, 5% sucrose, 0.1% TWEEN™ 20, 2 mM MgCl$_2$, 0.15 M NaCl and 0.1% NaN$_3$, then dried overnight at room temperature. Final drying was done in vacuum chamber.

Dried membrane with a polyester mobilization zone and application zone was laminated between two adhesive-coated mylar sheets from Adhesive Research, Inc. (Glen Rock, Pa.); Arcare 8259 for back lamination and Arcare 7843 for top lamination. The laminated membrane was cut into individual strips, 4 mm wide.

As sample, 150 μl of theophylline control at different theophylline levels, was applied on the application zone.

The theophylline negative strip showed deep color at the lower trap and almost no color at the upper trap. The reland trap can efficiently bind all unbound monoclonal antibody. As theophylline levels increased, the strips showed decrease of color at the lower trap and increase of color at the upper trap. High positive theophylline samples resulted in color only at the upper trap. Color density at each trap was measured by Gretag D 19C Remission Densitometer (from Switzerland). Results are in Table 6 below.

TABLE 6

Results of Theophylline Dipstick Assay

| THEOPHYLLINE LEVEL μg/ml | UPPER TRAP | LOWER TRAP | RATIO UPPER/LOWER |
| --- | --- | --- | --- |
| 0 | 0.025+ | 0.21 | 0.12 |
| 0.1 | 0.04 | 0.18 | 0.22 |
| 1.0 | 0.05 | 0.11 | 0.45 |
| 10.0 | 0.05 | 0.01+ | 5.00 |

+visually no color is observed.

B. Another variation of this format is a dipstick with a different second trap (upper trap). Strips are made exactly the same way as in A above, but carboxypropyl dimethyl xanthine (CPDMX) bovine gamma globulin conjugate was used as an upper trap. CPDMX, the ligand used as a immunogen, has much higher affinity to anti-theophylline antibody than theophylline-7-acetate. The above conjugate was coated in the form of an 8 mm wide band along the nylon membrane at 2 mm distance above the first trap. 200 μl of coating solution at concentration 1 mg/ml of 0.05 M phosphate buffer, pH 7.5 was used to make a band 8 mm long. Coated membrane was assembled the same way as in (A) variation.

Dipsticks were made and run with theophylline controls the same way as for (A) variation. Measurement of color at both traps is in Table 7 below.

TABLE 7

Results of Theophylline Dipstick Assays

| THEOPHYLLINE LEVEL in μg/ml | UPPER TRAP | LOWER TRAP | RATIO UPPER/LOWER |
| --- | --- | --- | --- |
| 0 | 0.005 | 0.1825 | 0.03 |
| 0.1 | 0.045 | 0.229 | 0.20 |
| 1.0 | 0.140 | 0.185 | 0.76 |
| 10.0 | 0.140 | 0.030 | 4.67 |

C. Another theophylline dipstick composition is a variation of (B). The upper trap is, as in B, carboxypropyldimethyl xanthine (CPDMX) bovine gamma globulin conjugate, but the conjugate is first absorbed on latex and then the latex-conjugate is deposited on the strip membrane.

CPDMX-bovine gamma globulin conjugate was absorbed to latex in the following manner: 25 μl of 10% latex (size 1.024 micrometer, from Bangs Lab., Carmel, Ind.) was added to 150 μg of protein in 0.05 M sodium phosphate buffer, pH 7.5. After gentle rocking overnight at room temperature, the latex was washed two times with 0.5% bovine serum albumin in the buffer and reconstituted in 100 microliters of the washing buffer. Strips were prepared as described above except that nitrocellulose STHF 0400 (from Millipone Corp. Bedford, Mass.) was utilized in place of nylon. Latex coating solution contained CPDMX conjugate at 1 mg/ml.

Strips were run with theophylline controls, 0 and 3 μg/ml, the same way as for (A) and (B) variations. Measurements of absorbance at both traps were done by diode ray spectrophotometer (Ocean Optics, Dunedin, Fla.).

This experiment illustrates that by increasing the valence of the trap material by absorbing the thcophylline immunogen ligand-bovine gamma globulin conjugate to latex, it could bind a far greater amount of low valence gold particles, i.e., gold particles not retained by reland trap in the presence of 3 μg/ml of theophylline. Results are presented in FIG. 6.

The results clearly show a big increase in binding as the valence of the trapping particle is increased.

EXAMPLE 9

Bone Alkaline Phosphatase Dipsticks

Dipsticks were made and assembled as described in Example 3 using a monoclonal antibody labelled with gold and deposited on polyester membrane.

The nylon membrane and polyester membrane were mounted between adhesive-coated plastic as described for other examples.

Assay Components

1. First trap (lower)—Non-competitive Trap for unbound antibody.

Alkaline Phosphatase from human placenta (PLAP) (Sigma) was used as a reland trap. PLAP at a concentration 2 mg/ml of 0.05 M phosphate buffer, pH 7.5 was coated on nylon membrane in the form of 5 mm wide band.

2. Second trap (upper)—Trap for bound antibody.

Goat anti-mouse IgG, Fc (from Jackson Immunoresearch) was used as the trap for bound antibody. The nylon membrane was coated at an anti-antibody concentration of 0.2 mg/ml, in the form of a 3 mm wide band, 4 mm distal to the first trap.

3. The coated nylon membranes were blocked by blocking buffer consisting of 0.1% gelatin in 0.05 M Tris/HCl, pH 8.0.

4. Gold—Monoclonal Antibody.

100 μg of a mouse monoclonal antibody to bone alkaline phosphatase, B4-78. The B4-78 antibody showed no cross-reactivity with human placental alkaline phosphatase up to 128UIL. (The B4-78 monoclonal antibody was developed by Dr. Jerry Katzman and was obtained from the Department of Biological Sciences, University of Iowa, Iowa City, Iowa 52242, under contract N01-HD-2-3144 from the NICHD, from which it is available to the public as well as from the Developmental Studies Hybridoma Bank Depository maintained by the Department of Pharmacology and Molecular Sciences, John Hopkins University School of Medicine, Baltimore, Md. 21205), was conjugated to 10 ml of 0.01% of gold particles, size 20 nm (Zymed Lab., Inc., San Francisco, Calif.) in 2.5 mM borate buffer, pH 9.0. After one hour, bovine serum albumin was added to a final concentration 0.1%, and the preparation was concentrated about 10 times with centrifugal concentrators (Microsep from Filtron, Northborough, Mass.). Finally, the gold preparation was spun down and the gold particles resuspended in 1 ml of diluent consisting of 0.25 M Tris/HCl, pH 8.2, 0.1% ovalbumin and 0.05% sodium azide. 100 µl of gold—mab conjugate working solution was measured at microtiter plate reader, S.L.T. 340 ATC. O.D. at 550 mm was 1.646.

The polyester membrane was coated with the gold—mab conjugate after completion of gold conjugation. The membrane was dried and stored with desiccant at 4 degrees Centigrade until dipsticks were assembled.

Assay Run

Individual dipsticks were placed into small test tubes containing 200 µl of bone or liver alkaline phosphatase standards in PBS buffer. Sample absorbed by the application zone wetted the mobilization zone and mobilized the gold particles which migrated with sample flow through the nylon membrane to the top of the strip.

Test Results

Samples consisted of human bone (BAP) and liver (LAP) alkaline phosphatase at levels of 0, 100 mU/ml, 300 mU/ml, 500 mU/ml, 1,000 mU/ml in PBS.

For 0 bone or liver alkaline phosphatase (BAP or LAP), the amount of color at both traps was similar.

For 100 mU/ml BAP and higher, the trap for bound, upper trap showed dose related increase in color.

For liver alkaline phosphatase (LAP) at level 100, 300, 500, and 1,000 mU/ml, there is no increase in color of the second or bound trap indicating that LAP does not cross-react with the receptor under the assay conditions.

Results are summarized below in Table 8. The values are the mean of two readings.

TABLE 8

Results Obtained with Alkaline Phosphatase Dipstick

| APase (mU/ml) | Lower (L) Mean Value | Upper (U) Mean Value | Ratio (U/L) |
| --- | --- | --- | --- |
| 0 | 0.07 | 0.08 | 1.04 |
| 00 | 0.07 | 0.06 | 0.86 |
| 100 (BAP) | 0.08 | 0.14 | 1.79 |
| 300 (BAP) | 0.08 | 0.16 | 2.04 |
| 500 (BAP) | 0.11 | 0.29 | 2.57 |
| 1000 (BAP) | 0.08 | 0.32 | 4.00 |
| 100 (LAP) | 0.08 | 0.08 | 1.00 |
| 300 (LAP) | 0.07 | 0.06 | 0.93 |
| 500 (LAP) | 0.11 | 0.09 | 0.84 |
| 1000 (LAP) | 0.08 | 0.09 | 1.08 |

EXAMPLE 8

Assay for Peptide Linked Pyridinoline ("PLP")

A. GOLD—ANTI PLP ANTIBODY CONJUGATE PREPARATION.

Colloidal gold, made by Serex (Maywood, N.J.) according to Roth J. was conjugated to monoclonal anti-peptide linked pyridinoline (PLP) antibody 93A (ATCC# HB-12254) according to the conjugation procedure described by Roth J., as follows (see example 2):

The gold preparation was spun down for 15 minutes at 6,000 RPM. Supernatant with unabsorbed antibody was discarded and the particles were resuspended in 1 ml of diluent consisting of 0.025 M. Tris/HCl buffer, pH 8.2, 0.1% bovine serum albumin, and 0.05% sodium azide. 100 µl of gold-anti PLP antibody conjugate working solution was measured with a microtiter plate reader, S.L.T.340ATC. O.D. at 550 nm was 1.8 to 2.2.

B. THE MEMBRANE

A. Using the above general procedure in Example 3 for making the nylon membrane supported on mylar strips, a piece of nitrocellulose (Millipore STHF040000) was cut into a rectangular piece 8 cm by 18 cm. Using a BIODOT BIOJET™ dispenser (Irvine, Calif.) and applying a first trap, i.e., a trap for the unbound material, was laid down on the membrane strip in the form of a band 5 mm wide approximately 1.5 cm from the bottom of the membrane. The trap material was the reland SJZ-22 conjugated to rabbit gamma globulin at a concentration of 1 mg/ml in 0.05 M-phosphate buffer at pH 7.5.

The second trap, that is the upper trap or the trap for bound material, was laid down in the form of a 5 mm wide band 2 mm distal to the first trap. The coating solution for this second trap was goat anti-mouse IgG, H+L antibody from Jackson Immunoresearch Lab (West Grove, Pa.) used at a concentration of 0.25 mg/ml in 0.05 M phosphate buffer pH 7.5. The third trap was goat anti-mouse IgGFc (Jackson). After each deposition of the trap, the membrane was dried for several hours at room temperature and then soaked for 30 minutes in Serex blocking buffer. After the blocking solution was applied, the strip was dried overnight at room temperature in a forced air oven.

This trap is not specific enough to trap all the gold passing through the trap. Polyclonal antibody raised to 93A on gold as immunogen or sera raised to 93A on gold reacted with (urine) analyte as immunogen can also be or alternatively be used.

C. STRIP ASSEMBLY

A gold membrane including a 2.1 cm×16 cm piece of POREX™ X-4588 DBS membrane carrying gold particles conjugated to anti-PLP antibody prepared as described above was used. 160 microliters of gold conjugate was applied along 16 cm of the Porex piece and dried for 2 hours. The gold membrane was then placed at the bottom of the nitrocellulose membrane overlapping it by 2 mm. The strip was then laminated between two plastic supports using the BIODOT™ custom clamshell laminator. A strip of plastic designated ARCARE™ 8259 from Adhesive Research, Inc. (Glen Rock, Pa.) was applied to the backside of the prepared nitrocellulose membrane.

The entire assembly was then top laminated with Arcare 7843, also from Adhesive Research, Inc. (Glen Rock, Pa.) which uses the same adhesive, but a different mylar thickness. The top lamination was applied leaving 5 mm of the proximal area of the gold membrane uncovered. Depending on preferences and the assay, the entire membrane assembly including the application zone and the mobilization zone can be covered, leaving only the edge of the device open or available for applying sample to the device or in some cases dipping the strip into the sample.

After the entire laminated assembly was prepared, it was cut with an AZKO™ knife (Azko, Elmwood Park, N.J.) into individual strips 5 mm wide. The membrane strips were placed on the mylar in such a manner as to provide 3 mm adhesive on all sides of the membrane and, in this case, the mylar can serve as the packaging of the strip. An 11 mm×5 mm Transpad was placed over an exposed part of the gold membrane and stapled on for sample transfer. This pad can be held by the adhesive or stapled.

D. ASSAY RUN

Individual units were dipped into appropriate size test tubes or cups containing urine PLP controls or urine samples with different PLP levels for 3 seconds and placed in the UMM reflectometer immediately.

E. TEST RESULTS

At low levels of bone resorption marker a majority of the gold labeled anti PLP reacts with lower reland trap and little color was at the upper trap site. With increasing PLP levels, the color of the lower trap appears gradually lighter to almost complete disappearance for very high PLP levels. Absorbance at each trap was measured by diode ray spectophotometer (Ocean Optics; Dunedin, Fla.). Results are summarized below in Table 9.

TABLE 9

Results Obtained with Alkaline Phosphatase Dipstick.

| PLP LEVEL mM/L | UPPER BAND* | LOWER BAND* | RATIO (L/U) |
|---|---|---|---|
| 0 | 0.268 | 0.230 | 0.86 |
| 63 | 0.259 | 0.175 | 0.68 |
| 125 | 0.267 | 0.110 | 0.41 |
| 250 | 0.259 | 0.081 | 0.31 |
| 500 | 0.299 | 0.084 | 0.28 |
| 1,000 | 0.302 | 0.068 | 0.23 |

*The values are the mean of three readings

We claim:

1. A chromatographic device for determining the presence or amount of analyte in a sample comprising:
   a) a sample receiving site,
   b) a mobilization zone in liquid communication with and spatially distinct from the sample receiving site, wherein the mobilization zone comprises liquid-mobilizable labelled multivalent receptors, wherein the liquid-mobilizable labelled multivalent receptors have at least one binding site which binds to the analyte in the sample to form receptor:analyte complexes, and
   c) at least two separate trap zones downstream of and in liquid communication with the mobilization zone, wherein each trap zone comprises at least one different immobilized ligand which binds to an analyte binding site of the liquid-mobilizable labelled multivalent receptors with an avidity or affinity different than the avidity or affinity of the immobilized ligand to an analyte binding site of the liquid-mobilizable labelled multivalent receptors in the other trap zone, wherein the avidity or affinity of the immobilized ligand increases in each trap zone further downstream of the mobilization zone, and wherein the presence or amount of the analyte in the sample is determined from the distance over which the receptor:analyte complexes migrate through the trap zones.

2. The device of claim 1 wherein the immobilized ligands of at least one of the trap zones comprise relands which non-competitively bind to the liquid-mobilizable labelled multivalent receptor in the presence of analyte under conditions in which the sample is reacted with the liquid-mobilizable labelled multivalent receptor, and
   wherein the immobilized ligand in monomeric form and the liquid-mobilizable labelled multivalent receptor bind with an association constant between $10^3$ $M^{-1}$ and $10^5$ $M^{-1}$.

3. The device of claim 1 wherein at least one of the immobilized ligands can compete with the analyte for binding to the liquid-mobilizable labelled multivalent receptor.

4. The device of claim 1 further comprising an affinity trap zone containing immobilized antibodies binding to the liquid-mobilizable labelled multivalent receptor.

5. The device of claim 4 wherein the immobilized antibodies are immunoreactive with heavy or light chains of antibody.

6. The device of claim 1 wherein the immobilized ligands are in different trap zones of the device which are in liquid communication with the sample receiving zone and mobilization zone, wherein a receptor:analyte complex moves to the first trap zone with immobilized ligand binding to the receptor:analyte complex having the lowest number of analyte molecules bound to the liquid-mobilizable labelled multivalent receptor, then moves to a second trap zone with immobilized ligand binding to a receptor:analyte complex having a higher number of analyte molecules bound to the liquid-mobilizable labelled multivalent receptor.

7. The device of claim 6 comprising multiple trap zones having the same immobilized ligand therein at different densities.

8. The device of claim 1 wherein each immobilized ligand is selected from the group consisting of relands, molecules which do not effectively compete with analyte for binding to the liquid-mobilizable labelled multivalent receptor, competitive ligands, and immunogens.

9. The device of claim 1 wherein the sample receiving site, the mobilization zone and the trap zones are on a membrane and the membrane is at least partially enclosed in a laminat, except for the sample receiving site, to control flow of reactants through the trap zones.

10. The device of claim 9 including proximal and distal ends, wherein the sample receiving site is adjacent the proximal end and the mobilization zone is between the distal end and the sample receiving site, wherein the device further comprises a wicking material attached at the proximal end for absorbing or filtering the sample.

11. The device of claim 1 wherein the liquid-mobilizable labelled multivalent receptors are labeled with a label or labels selected from the group consisting of colored or fluorescent dyes, chromogens, colloidal gold, enzymes, and latex.

12. The device of claim 1 further comprising a means for correlating the amount or the presence of the trapped analyte:multivalent receptor:complexes, the trapped unbound liquid-mobilizable labelled multivalent receptor, or both, to the presence of or the amount of analyte in the sample.

13. The device of claim 1 wherein multiple analyte binding domains are bound to a particle to form the liquid mobilizable multivalent receptors.

14. The device of claim 1 wherein the analyte binding domains of the liquid-mobilizable labelled multivalent receptor on any one particle are antibodies which are all reactive with the same epitope of analyte.

15. The device of claim 1 wherein the immobilized ligands are in different trap zones which are in liquid communication with the sample receiving zone and mobilization zone, wherein the affinity of the different trap zones is increased by increasing the affinity of the immobilized ligands for the receptors.

16. The device of claim 1 wherein at least one of the immobilized ligands is multivalent.

17. The device of claim 16 wherein the affinity of the trap zone is increased by increasing the valency of the immobilized ligand.

18. The device of claim 1 further comprising a built-in control.

19. The device of claim 1 wherein the mobilization zone is of sufficient length that analyte in the sample complexes with the liquid-mobilizable labelled multivalent receptors prior to reaching a first trap zone.

20. A chromatographic device for detecting an analyte in a sample comprising:
   a) a sample receiving site,
   b) a mobilization zone downstream of and in liquid communication with the sample receiving site,
      the mobilization zone comprising liquid-mobilizeable labelled receptors binding to analyte in the sample to form receptor:analyte complexes, and
   c) at least one trap zone downstream of and in liquid communication with the mobilization zone
      wherein at least one trap zone comprises an immobilized ligand which is non-competitive with the analyte bound by the receptor under the conditions used to interact the sample with the immobilized ligands, the association constant of the non-competitive ligand in monomeric form and the receptor being between $10^3$ $M^{-1}$ and $10^5$ $M^{-1}$,
      whereby when analyte present in the sample forms receptor:analyte complexes, the non-competitive ligand in the trap does not bind receptor:analyte complex and the receptor:analyte complexes migrate through the trap zone, but wherein the non-competitive ligand does bind to the liquid-mobilizable labelled receptor not bound to analyte the liquid-mobilizable labelled receptor does not migrate through the trap zone, and
   d) a means for correlating the amount of the receptor:analyte complex or the trapped unbound liquid-mobilizeable labeled receptor or both to the amount of analyte in the sample.

21. The device of claim 20 wherein when there is more than one trap zone, at least one of the trap zones which bind receptor:analyte complex comprises antibody immunoreactive with the liquid-mobilizeable labelled receptor.

22. The device of claim 21 further comprising a trap zone containing immobilized ligands competitive with analyte for receptor.

23. The device of claim 20 wherein the sample receiving site, the mobilization zone, the non-competitive ligand trap zone, and the detection zone are present in a unitary continuous strip.

24. The device of claim 20 wherein the trap zones binding receptor:analyte complex are selected from the group consisting of traps containing ligands competitive with analyte for receptor, immunogen ligand affinity traps, and traps containing ligands for binding antibody.

25. The device of claim 20 wherein the sample receiving site further comprises a hydrophilic material for absorbing or filtering the sample.

26. The device of claim 20 wherein the reland is formed by substituting neutral groups for ionic groups in analyte.

* * * * *